US006343435B1

(12) United States Patent
Moquet et al.

(10) Patent No.: US 6,343,435 B1
(45) Date of Patent: Feb. 5, 2002

(54) AGARICUS BISPORUS HYBRIDS, OBTAINING THEM, AND THEIR USE

(75) Inventors: Frederic Moquet, Saint Magne; Jean-Marc Olivier, Beautiran; Regis Vedie, Saint Paterne Racan; Philippe Callac, Villenave D'Ornon, all of (FR)

(73) Assignees: Institut National de la Recherche Agronimique, Paris; C.T.C. - Centre Technique du Champignon, Saint Paterne Racan, both of (FR)

( * ) Notice: Subject to any disclaimer, the term of this patent is extended or adjusted under 35 U.S.C. 154(b) by 0 days.

(21) Appl. No.: 09/355,248

(22) PCT Filed: Jan. 27, 1998

(86) PCT No.: PCT/FR98/00139

§ 371 Date: Oct. 21, 1999

§ 102(e) Date: Oct. 21, 1999

(87) PCT Pub. No.: WO98/32327

PCT Pub. Date: Jul. 30, 1998

(30) Foreign Application Priority Data

Jan. 27, 1997 (FR) ............................. 97 00834

(51) Int. Cl.⁷ .......................... A01G 1/04; A01H 15/00
(52) U.S. Cl. ....................................................... 47/1.1
(58) Field of Search .................. 47/1.1, 58.1; 800/260, 800/297

(56) References Cited

U.S. PATENT DOCUMENTS

| 4,079,543 A | | 3/1978 | Stoller |
| 4,608,775 A | * | 9/1986 | Elliot et al. ................. 47/1.1 X |
| 4,996,390 A | | 2/1991 | Dahlberg |
| 5,304,721 A | | 4/1994 | Kerrigan et al. |

FOREIGN PATENT DOCUMENTS

| FR | 2 549 346 A1 | 1/1985 |
| FR | 2 603 767 A1 | 3/1988 |
| FR | 2 676 158 A1 | 11/1992 |
| FR | 2 696 187 A1 | 4/1994 |
| FR | 2 723 506 A1 | 2/1996 |

OTHER PUBLICATIONS

La Maison Rustique–Flammarion (Paris, France), *The Cultivation of Mushrooms*, (1988), Published by Somycel.
J.M. Olivier et al., *La culture des champignons [Mushroom Production]*, (1991), published by Armand Colin.
V.S. Pahil et al., *The testing and improvement of high temperature, wild Argaricus strains for use in tropical and subtropical climates*, Science and Cultivation of Edible Fungi, Maher (ed.), 1991, pp. 589–599.
S.L. Horna et al., *Selection of Lines of Agaricus brunnescens Peck for Higher Production Temperatures*, HortScience 18(6), pp. 866–868 (1983).
P.B. Flegg, *Effect of Temperature on the Mushroom AGARICUS BISPORUS: A Brief Review of Twenty Years of Research*, XP002046578, pp. 65–67.

* cited by examiner

Primary Examiner—Peter M. Poon
Assistant Examiner—Jeffrey L. Gellner
(74) Attorney, Agent, or Firm—Oliff & Berridge, PLC

(57) ABSTRACT

The invention concerns intraspecific hybrids of *Agaricus bisporus* capable of bearing fruit at relatively high temperature and without roughing-in, and the method for obtaining them consisting in a step of cross-breeding in particular between a first and a second *Agaricus bisporus*, one of which at least belongs to the *burnettii* variety, and a step of selecting the resulting hybrids having the characteristics mentioned above. The cultivation of the resulting hybrids is easier and less expensive than the standard method of cultivating mushrooms.

24 Claims, No Drawings

AGARICUS BISPORUS HYBRIDS, OBTAINING THEM, AND THEIR USE

The invention relates to novel *Agaricus bisporus* hybrids, a method of obtaining them, and their use in mushroom growing,.

It is known that growing the mushroom *Agaricus bisporus*, also called cultivated mushroom, comprises a certain number of steps, which are recalled herein-below.

A first step (composting) consists in the preparation of a substrate based on straw, horse manure and, if appropriate, nitrogen-containing additives, in order to obtain, by fermentation, a substrate (compost) which contains nutrient elements which can be used by the mycelium during the multiplication phase. The duration of this composting step is around 2 to 3 weeks. In general, the composting step is completed by a step called pasteurization, which consists in improving the quality of the compost by directed fermentation in special rooms, in general over 5 to 7 days. The following step is inoculation, which consists in seeding the culture substrate as obtained with "spawn", that is to say mycelium multiplied on cereal grains. The inoculation rate specifies the ratio of spawn weight to compost weight. This inoculation rate is generally over 0.5% and under 1%. The next step is the incubation, during which the mycelium multiplies and progressively colonizes the culture substrate. This incubation phase is carried out either on special controlled-environment premises or in a culture cave system at a substrate temperature of around 24–26°. The average time of the incubation phase is approximately 14 days. The next operation which is carried out is called casing, which consists in covering the culture substrate with a layer of a casing material which generally, in particular in France, consists of a mixture of limestone (for example tufa) and peat. This layer has a thickness of generally around 3 to 5 cm. To enhance the formation of fruiting bodies, a thermal shock technique is used which consists in lowering the ambient temperature to around 16–17° C. with a substantial renewal of air and regular watering. This latter phase of inducing the formation of fruiting bodies is sometimes preceded, just after casing, by a phase called prefructification, which consists in maintaining an ambient temperature of around 24° C. with slight renewal of air over 8 to 10 days.

The mushrooms are harvested from successive emergences (termed "flushes"). The so-called first-flush harvest can generally be carried out three weeks after casing. In general, it is possible to harvest 4 to 5 flushes over a period of 5 to 7 weeks after the beginning of the first harvest. The total harvest yield can be expressed by weight of mushrooms per 100 kg of compost. The average yields are approximately 30%.

Thus, growing cultivated mushrooms is very restricting, in particular concerning the temperature regulation, which leads to a noteworthy consumption of energy and thus to considerable costs.

The casing step is also expensive in terms of labour and casing material.

If the formation of the cultured mushroom is to be achieved, however, the casing operation cannot be dispensed with. The same applies to the thermal shock step.

The following works on methods of growing cultivated mushrooms can be cited in particular: J. Delmas, Les champignons et leur culture [Mushrooms and their production], published by La Maison Rustique—Flammarion (Paris, France); The cultivation of Mushrooms (1988), published by Somycel; and Olivier J. M. et al., La culture des champignons [Mushroom production] (1991), published by Armand Colin. With reference to the casing step and the fact that it is required for obtaining the formation of fruiting bodies, W. A. Hayes, The Casing Layer, published by W. S. Maney and Son Ltd., Leeds (Great Britain) may also be cited.

The materials used for casing are very varied. Apart from peat and mixtures of peat and limestone rock, there may be mentioned clay, gypsum, sand and the like. The use of layers of synthetic materials or natural or synthetic polymeric materials which are capable of retaining water has also been recommended. In this matter, the patents, or patent applications, FR-2 549 346, FR-2 603 767, FR-2 676 158, FR-2 723 506 and U.S. Pat. No. 4,079,543 may be cited in particular.

It has now been found that it is possible to obtain Agaricus hybrids which can form fruiting bodies without casing and which can be grown under conditions which are less constraining as regards temperature regulation, because it has been found that certain hybrids obtained by hybridizing strains of *Agaricus bisporus* with *Agaricus bisporus* var. *burnettii*, or progeny or hybridization products of this variety, are capable of forming fruiting bodies without casing and can, moreover, form fruiting bodies without thermal shock. Moreover, the invention allows hybrids to be obtained whose mycelia are capable of multiplying on substrates at higher temperatures without losing their capability of forming fruiting bodies.

These novel hybrids can thus be grown while substantially reducing labour and energy costs.

Moreover, the invention makes it possible to grow cultivated mushrooms even in countries with a hot climate, where it was hitherto impossible to grow them profitably.

The invention relates to a hybrid mycelium of *Agaricus bisporus* having at least one of the following phenotypic, stable and genetically transmissible traits:

after multiplication on a usual culture substrate and penetration of this substrate, it is capable of forming fruiting bodies without casing;

after multiplication on a usual culture substrate and penetration of this substrate, it is capable of forming fruiting bodies at a substrate temperature of 26° C. or above;

after multiplication on a usual culture substrate and penetration of this substrate, it is capable of forming fruiting bodies at an ambient temperature of 24° C. or above;

it is capable of growing on a usual culture substrate at a substrate temperature of 30° C. or above.

The term "hybrid mycelium" designates in the present application:

a) either a mycelium which originates from at least one hybridization between two parental strains of *Agaricus bisporus*, that is to say which originates from the combination via fusion of cytoplasms (plasmogamy) of two homokaryons which themselves originate from two distinct heterokaryotic parent strains, b) or a mycelium which originates from a spore produced by the fruiting bodies of a mycelium as defined under a) above, c) or a mycelium which originates from a protoplast obtained from a mycelium as defined under a) and/or b) above.

Mycelia according to the invention are thus intraspecific hybrids.

When the hybrid mycelium according to the invention is capable of growing on a usual culture substrate at a temperature of, for example, 30° C. or above, it must be understood that it is capable of penetrating this substrate at this temperature, without, however, losing its capability of forming fruiting bodies, which means, in particular, that fruiting bodies are produced within normal time limits (not more than 5 to 6 weeks after inoculation), that the yield by weight (weight of harvested mushrooms per 100 kg of compost) over 5 weeks of harvest is at least equal to 10%, and that the mushrooms produced have a normal appearance (morphology, dimensions).

The usual culture substrates are well known and are described, for example, in the abovementioned works. They are generally composts based on horse manure and straw.

The invention relates in particular to a hybrid mycelium as described hereinabove which is capable of forming fruiting bodies at a substrate temperature of 28° C. or above and/or which is capable of forming fruiting bodies at an ambient temperature of 26° C. or above, in particular at 28° C. or above, and/or which is capable of multiplying on a usual culture substrate and of penetrating this substrate at a substrate temperature of 32° C. or above without losing the capability of forming fruiting bodies, and/or which is capable of forming fruiting bodies without casing with a sporophore yield of at least 10 kg per 100 kg of culture substrate over a period of 5 weeks, starting at the beginning of the formation of fruiting bodies.

The hybrid mycelium according to the invention is generally heterokaryotic, but may also originate from a heterokaryotic or even homokaryotic single-spore culture of such a hybrid. It has indeed been discovered that, surprisingly, certain homokaryotic (that is to say haploid) mycelia which originate from hybrids according to the invention were capable of forming fruiting bodies; see experimental part hereinbelow.

The invention covers the sporophores which originate from the formation of fruiting bodies of a hybrid mycelium as defined hereinabove, as well as heterokaryons or homokaryons which originate from such a mycelium or such a sporophore.

The invention also relates to a method of growing *Agaricus bisporus*, which comprises a step in which mycelium is multiplied on a usual culture substrate and penetrates this substrate, followed by a step in which fruiting bodies are formed, in which this mycelium is a hybrid mycelium as defined above and exhibiting at least one of the following traits:

the process does not comprise a casing step;

the step in which the mycelium is multiplied on the substrate and the substrate is penetrated is carried out at a substrate temperature of 26° C. or above;

the step in which fruiting bodies are formed is carried out at an ambient temperature of 24° C. or above.

In particular embodiments, the production process according to the invention can also exhibit the following features, either alone or in combination:

the step in which the mycelium is multiplied and the substrate is penetrated is carried out at a substrate temperature of 28° C. or above, in particular at 30° C. or above;

the step in which fruiting bodies are formed is carried out at a substrate temperature of 28° C. or above;

the step in which fruiting bodies are formed is carried out at an ambient temperature of 26° C. or above, in particular at 28° C. or above;

the process is carried out without the step of a thermal shock after the step in which the mycelium is multiplied.

The invention also relates to a method of obtaining a hybrid mycelium, sporophores or hetero-karyons or homokaryons as defined hereinabove, the process being characterized in that it comprises at least one hybridization step between a strain of *Agaricus bisporus* or a hybrid progeny of this strain and an *Agaricus bisporus* var. *burnettii* or a hybrid progeny of this variety, and in that those hybridization products are selected which exhibit the desired phenotypic trait. It follows from this that these phenotypic traits are genetically transmissible and are expressed in a stable fashion after having been transmitted.

The desired phenotypic character can be either one of the phenotypical traits mentioned in the definition of the hybrid mycelium according to the invention or a combination of two or more of these traits.

The variety burnettii of the species *Agaricus bisporus* has been described by Callac et al., Mycologia 85 (5), 835–851 (1993).

The hybridization steps can be carried out in a manner known per se. They are facilitated by the fact that, when *Agaricus bisporus* var. *burnettii* is hybridized with any strain of *Agaricus bisporus*, they produce hybrids whose spores are mostly homokaryotic; see, in this context, document WO 94/07357 and the U.S. Pat. No. 5304721.

To carry out the hybridization step in order to obtain what has been described, the *Agaricus bisporus* var. *burnettii* which may be used is, in particular, strain JB3 ms, which has been deposited at CNCM (France) on Jan. 23, 1997, under the number I-1811, and strain JB162 ms, which has been deposited at CNCM on Jan. 23, 1997, under the number I-1812.

An *Agaricus bisporus* which may be used as the first *Agaricus bisporus* (as defined in the process of obtaining it which has been described hereinabove) is, for example, one which does not belong to the variety *burnettii*, or a hybrid progeny of such an *Agaricus bisporus*. In particular, different strains of commercially obtainable mushrooms can be used, such as, for example, HU1. The strain HU1, which is also termed U1, is a commercial strain obtained from Station de Horst (Netherlands) and distributed by Sylvan-Somycel. This first *Agaricus bisporus* can also belong to the variety *burnettii* or be a hybrid progeny of this variety.

To carry out hybridization strategies, it is possible to use, in particular, the methods described in the PCT document WO 94/07357, which corresponds, in particular, to the U.S. Pat. application Ser. No. 08/403750, whose description is incorporated in the present description by way of reference.

The examples which follow illustrate the invention.

EXAMPLES

Example 1

A first homokaryon of *Agaricus bisporus* var. HORST® U1, which is commercially available from Sylvan-Somycel, was isolated by the protoplast method.

This homokaryon was propagated in the usual manner on usual compost to obtain a homokaryotic mycelium and then hybridized with a homokaryotic mycelium which originates from the strain JB3. The heterokaryon obtained was grown on the usual compost. After incubation for 14 days at 24° C., a casing is made with a mixture of powdered tufa and peat (2:1 by volume). The tufa is a natural limestone.

The culture is placed in a fructification chamber at 16° C. The sporophores appear 16 days after casing.

The resulting first-generation hybrid provides fruiting bodies whose basidia are predominantly tetrasporous. The spores obtained are germinated on Raper medium (reference: Raper et al. (1972) Mycologia, 64, 1088–1117). The mycelia which originate from germinated spores were isolated and their homokaryotic character was confirmed by confrontation tests with tester homokaryons and by genotypic analyses with the aid of enzymatic and molecular markers.

A homokaryotic monosporous progeny of this tetrasporous hybrid was hybridized with a second homokaryon of strain U1, this second homokaryon being of the opposing mating type of the first homokaryon mentioned hereinabove and used previously as parent of the first-generation hybrid strain. Thus, a second-generation hybrid whose fruiting bodies, obtained as above, are tetrasporous.

112 spores which originate from the fruiting body of the second-generation hybrid were isolated and germinated as above.

The resulting mycelia were used for performing hybridizations with a compatible homokaryotic mycelium which originates from a single spore of strain JB162 ms.

This gives rise to a third generation of hybrids.

Study of 3rd-Generation Hybrids

First tests were carried out on 36 3rd-generation hybrids.

The tests were performed in boxes containing 15 kg of the usual compost (horse manure+straw).

Inoculation was done at a rate of 1%.

The compost temperature during inoculation was 28° C.

The ambient temperature during the growth period of the mycelium and the penetration of the compost was set at 25° C. (relative humidity 95%).

14 days after inoculation, casing was performed with a usual casing material (limestone and peat at a ratio of 3:1 by volume).

After casing, the ambient temperature was lowered to 16° C. (relative humidity 92%).

In 11 of the 36 hybrids studied, the formation of fruiting bodies was observed even before casing, thus at an ambient temperature of 25° C.

The reproducibility of the phenomenon observed was checked by reculturing strains which had formed fruiting bodies without casing, including on composts which differed from the compost used in the previous experiments (for example horse manure without added straw).

The parent strains (second-generation hybrids and JP162 ms) which were grown under the same conditions did not form fruiting bodies without casing.

In other experiments on 32 third-generation-hybrids (of which some had already been tested in the test described hereinabove), it was observed that 25 hybrids formed fruiting bodies without casing.

In several cases, the cumulative mushroom yield of cultures without casing over a period of up to five weeks after inoculation is higher than the cumulative yield of cultures of the same hybrids which have been cased two weeks after inoculation.

Moreover, the formation of fruiting bodies without casing was observed on substrates whose temperature was above 28° C. and at ambient temperatures which were also above 28° C.

Also, the formation of fruiting bodies without casing under the same conditions as above was observed on different third-generation-hybrids obtained by hybridizing homokaryons of the second-generation hybrid with homokaryotic mycelia which originated from single spores of strain JB162 ms, the mycelia being other than the homokaryotic mycelium used for obtaining the above-described third-generation hybrids.

Other third-generation hybrids obtained by hybridizing the second-generation hybrid with an *Agaricus bisporus* var. *burnettii* strain other than JB162 have also given rise to fruiting bodies without casing under the same conditions as above.

Moreover, it has been observed that homokaryotic mycelia which originated from single-spore cultures of hybrids derived from JB162 ms are capable of forming fruiting bodies after incubation on the usual compost at a compost temperature of 28–30° C., with or without casing.

The homokaryotic state of these mycelia and of these fruiting bodies was checked on chromosome markers by RFLP after amplification by PCR.

Moreover, the mycelial growth of some third-generation-hybrids at a substrate temperature which has reached 35° C. one week after inoculation was tested. The mycelium had developed well, and, finally, fruiting bodies were obtained at an ambient temperature of 25° C. without casing, starting from such a mycelium which had developed temporarily at 35° C.

The effect of a low-temperature thermal shock was also studied. Culture containers containing 7 kg of compost were placed in a cold chamber at 4° C. for 14 hours, seven days after inoculation.

In comparison with the containers which had remained at 25° C., one day's delay in the formation of fruiting bodies was observed on the containers which had undergone low-temperature treatment. The low-temperature shock during incubation had therefore no noteworthy effect on the capability of forming fruiting bodies without casing.

Moreover, certain third-generation-hybrids were subsequently used in tests in which the inoculation rate was reduced (0.5% or 0.25% instead of 1%). While the yields were not affected, the first harvest was delayed by 4 to 6 days in comparison with the harvest obtained with an inoculation rate of 1%.

Comparison tests have demonstrated that the first-generation hybrid is not capable of forming fruiting bodies without casing and, equally, that hybrids obtained by hybridizing the second-generation hybrid with the first U1 homokaryon are not capable of forming fruiting bodies without casing.

In general, it must be finally noted that, when the process is not carried out in controlled-atmosphere chambers, for example when using caves, the absence of a casing may lead to surface desiccation of the compost, depending on the evaporation. Such a desiccation may adversely affect the formation of fruiting bodies. However, this problem can be remedied either by repeated moderate watering or by covering the compost with a plastic film until the fruiting bodies start to appear. It is also possible to cover the substrate in which the mycelium has developed by a layer of casing material in a reduced thickness (for example 0.5 to 2 cm).

Example 2

A third-generation hybrid strain obtained in the above example, which forms fruiting bodies without casing, is selected. It is grown and allowed to form fruiting bodies.

Spores which originate from the fruiting bodies thus obtained were isolated.

Most of these spores were homokaryotic. After germination, these homokaryotic spores were exposed to the first homokaryon of strain U1 which had been used for obtaining the first-generation hybrid (see Example 1). This gave rise to fourth-generation heterokaryotic hybrid mycelia.

The resulting fourth-generation hybrids as well as the strains which have originated from heterokaryotic spores of the third-generation hybrid selected hereinabove were grown in baskets containing 6.5 kg of compost.

The growth conditions were as follows:

Day 0: inoculation (1%).

After inoculation, the cultures were maintained at an ambient temperature of 25° C. (relative humidity: 90–93%).

Day 0+14: the ambient temperature was lowered to 16° C. (relative humidity: 90–92%).

The results were as follows.

Amongst 82 fourth-generation hybrid strains tested, 31 formed fruiting bodies without casing.

In other experiments, the hybrid strains were grown as above, but at a constant temperature of 25° C. (that is to say omitting the chilling to 16° C. on day 0+14). Again, the formation of fruiting bodies without casing was observed.

Thus, the trait of forming fruiting bodies without casing and at elevated temperatures is transmitted genetically.

Moreover, amongst the single-spore cultures isolated from the third-generation hybrid studied, 14 strains were found whose mycelia were heterokaryotic and which originated thus from heterokaryotic spores. Eleven of those were studied. From amongst these 11 mycelia, three formed fruiting bodies without casing.

What is claimed is:

1. *Agaricus bisporus* hybrid mycelium exhibiting the following phenotypic trait:

after multiplication on a culture substrate and penetration of this substrate, it is capable of forming fruiting bodies without casing.

2. Mycelium according to claim 1, exhibiting at least one of the following phenotypic traits:

after multiplication on a culture substrate and penetration of this substrate, it is capable of forming fruiting bodies at a substrate temperature of 26° C. or above;

after multiplication on a culture substrate and penetration of this substrate, it is capable of forming fruiting bodies at an ambient temperature of 25° C. or above;

it is capable of growing on a culture substrate at a substrate temperature of 32° C. or above.

3. Mycelium according to claim 1, characterized in that it is capable of forming fruiting bodies at a substrate temperature of 28° C. or above.

4. Mycelium according to claim 1, characterized in that it is capable of forming fruiting bodies at an ambient temperature of 26° C. or above.

5. Mycelium according to claim 4, characterized in that it is capable of forming fruiting bodies at an ambient temperature of 28° C. or above.

6. Mycelium according to claim 1, characterized in that it is capable of forming fruiting bodies without casing with a sporophore yield of at least 10 kg per 100 kg of culture substrate over a period of 5 weeks, starting at the beginning of the formation of fruiting bodies.

7. Mycelium according to claim 1, characterized in that this mycelium is heterokaryotic.

8. Mycelium according to claim 1, characterized in that this mycelium is homokaryotic.

9. Mycelium according to claim 8, characterized in that it is capable of forming fruiting bodies.

10. Sporophores which originate from fruiting bodies of a mycelium as defined in claim 1.

11. Heterokaryons or homokaryons which originate from a mycelium as defined in claim 1.

12. Method of growing *Agaricus bisporus*, which comprises a step in which mycelium is multiplied on a usual culture substrate and penetrates this substrate, followed by a step in which fruiting bodies are formed, in which this mycelium is as defined in claim 1 and in which the method does not comprise a casing step.

13. Method according to claim 12 characterized in that exhibits at least one of the following traits:

the step in which the mycelium is multiplied on the substrate and the substrate is penetrated and carried out at a substrate temperature of 32° C. or above;

the step in which fruiting bodies are formed is carried out at a substrate temperature of 26° C. or above;

the step in which fruiting bodies are formed is carried out at an ambient temperature of 25° C. or above.

14. Method according to claim 12, characterized in that the step in which fruiting bodies are formed is carried out at a substrate temperature of 28° C. or above.

15. Method according to claim 12, characterized in that the step in which fruiting bodies are formed is carried out at an ambient temperature of 26° C. or above.

16. Method according to claim 15, characterized in that said ambient temperature is 28° C. or above.

17. Method according to claim 12, characterized in that it does not comprise a temperature shock step after the step in which the mycelium is multiplied.

18. Method of obtaining a mycelium, sporophores, heterokaryons or homokaryons as defined in claim 1, characterized in that it comprises at least one hybridization step between a first *Agaricus bisporus* or a hybrid progeny thereof and an *Agaricus bisporus* var. *burnettii* or a hybrid progeny thereof, and in that among the hybridization products, those which exhibit the desired phenotypic trait are selected.

19. Method according to claim 18, characterized in that it comprises at least one hybridization step wherein the *Agaricus bisporus* var. *burnettii* is the strain deposited with CNCM under No. I-1811.

20. Method according to claim 18, characterized in that it comprises at least one hybridization step where the *Agaricus bisporus* var. *burnettii* is the strain deposited with CNCM under No. I-1812.

21. Method according to claim 18, characterized in that it comprises at least one hybridization step wherein said first *Agaricus bisporus* is selected among an *Agaricus bisporus* var. *burnettii*, a hybrid progeny of said variety and a commercial strain of *Agaricus bisporus*.

22. Method according to claim 21, wherein said commercial strain is the commercial variety U1.

23. Heterokaryons or homokaryons which originate from a sphorphore as defined in claim 10.

24. *Agaricus biosporus* hybrid mycelium, obtained by a method which does not comprise a temperature shock step after the step in which the mycelium is multiplied, exhibiting at least one of the following phenotypic traits:

after multiplication on a culture substrate and penetration of this substrate, it is capable of forming fruiting bodies at a substrate temperature of 26° C. or above, which develop normally without temperature shock;

after multiplication on a culture substrate and penetration of this substrate, it is capable of forming fruiting bodies at an ambient temperature of 25° C. or above, which develop normally without temperature shock;

it is capable of growing on a culture substrate at a substrate temperature of 32° C. or above.

* * * * *